US009945758B2

(12) United States Patent
Wendt

(10) Patent No.: US 9,945,758 B2
(45) Date of Patent: Apr. 17, 2018

(54) DEVICE AND METHOD FOR TESTING A VEHICLE

(75) Inventor: Axel Wendt, Stuttgart (DE)

(73) Assignee: ROBERT BOSCH GMBH, Stuttgart (DE)

(*) Notice: Subject to any disclaimer, the term of this patent is extended or adjusted under 35 U.S.C. 154(b) by 392 days.

(21) Appl. No.: 14/235,341

(22) PCT Filed: Jun. 12, 2012

(86) PCT No.: PCT/EP2012/061120
§ 371 (c)(1),
(2), (4) Date: Jun. 5, 2014

(87) PCT Pub. No.: WO2013/013877
PCT Pub. Date: Jan. 31, 2013

(65) Prior Publication Data
US 2014/0283608 A1 Sep. 25, 2014

(30) Foreign Application Priority Data
Jul. 28, 2011 (DE) .................. 10 2011 079 987

(51) Int. Cl.
G01M 17/007 (2006.01)
G01N 29/14 (2006.01)
G01N 29/04 (2006.01)

(52) U.S. Cl.
CPC .......... *G01M 17/007* (2013.01); *G01N 29/14* (2013.01); *G01N 29/045* (2013.01); *G01N 2291/106* (2013.01)

(58) Field of Classification Search
CPC ....... G01M 17/007; G06T 2207/20212; G06T 2207/20221; H04N 7/181; H04N 7/183; B60R 11/04
See application file for complete search history.

(56) References Cited

U.S. PATENT DOCUMENTS 5,300,925 A    4/1994 Depfenhart
6,550,332 B2*  4/2003 Lee .................... G10K 11/28
                                                   73/147

(Continued)

FOREIGN PATENT DOCUMENTS

CN    1842695 A    10/2006
CN    101029855 A   9/2007
(Continued)

OTHER PUBLICATIONS

International Search Report, PCT International Application No. PCT/EP2012/061120, dated Nov. 6, 2012.

*Primary Examiner* — Harshad R Patel
*Assistant Examiner* — Tran M Tran
(74) *Attorney, Agent, or Firm* — Norton Rose Fulbright US LLP; Gerard Messina

(57) ABSTRACT

A device for testing a vehicle includes at least one sound recording device, which is designed for recording the sound emitted by a vehicle to be tested, and an evaluation device, which is designed for evaluating the sound recorded by the at least one sound recording device. The device may include at least one image recording device, which is designed for recording at least one image of the vehicle to be tested, and a display device which is designed for representing the source(s) of the recorded sound in at least one image of the vehicle to be tested.

9 Claims, 4 Drawing Sheets

(56) References Cited

U.S. PATENT DOCUMENTS

| | | | | |
|---|---|---|---|---|
| 7,061,371 B2* | 6/2006 | Shockley | ............ | G01M 17/007 340/425.1 |
| 7,107,849 B2* | 9/2006 | Sugiyama | ............ | G01N 29/045 73/587 |
| 7,240,544 B2* | 7/2007 | Mallebay-Vacqueur | ............ | G01M 17/007 73/147 |
| 7,849,735 B2* | 12/2010 | Ochs | ........................ | G01M 3/24 73/117.01 |
| 8,067,719 B2* | 11/2011 | Herrera | .................... | H04N 7/18 250/208.1 |
| 8,380,389 B2* | 2/2013 | Wright | ................ | G01M 17/007 342/42 |
| 8,478,480 B2* | 7/2013 | Mian | .................... | G01M 17/013 250/316.1 |
| 8,649,932 B2* | 2/2014 | Mian | .................... | G01M 17/013 250/316.1 |
| 8,868,291 B2* | 10/2014 | Mian | .................... | G01M 17/013 250/316.1 |
| 9,509,960 B2* | 11/2016 | Mirza | ........................ | B60R 1/00 |
| 9,599,537 B2* | 3/2017 | DeAscanis | ............ | G01M 15/14 |
| 9,649,990 B2* | 5/2017 | Hoellmann | ............ | H04N 7/183 |
| 2002/0059832 A1 | 5/2002 | Lee | | |
| 2006/0137439 A1 | 6/2006 | Mallebay-Vacqueur et al. | | |
| 2007/0040911 A1* | 2/2007 | Riley | .................... | H04N 7/181 348/148 |
| 2010/0161255 A1 | 6/2010 | Mian et al. | | |
| 2014/0283608 A1* | 9/2014 | Wendt | .................... | G01N 29/14 73/587 |

FOREIGN PATENT DOCUMENTS

| | | |
|---|---|---|
| CN | 101419122 A | 4/2009 |
| CN | 201666815 U | 12/2010 |
| DE | 10157196 A1 | 5/2002 |
| DE | 102008034585 A1 | 2/2010 |
| EP | 2538210 A2 | 12/2012 |
| JP | 2006-201124 | 8/2006 |

* cited by examiner

DEVICE AND METHOD FOR TESTING A VEHICLE

FIELD

The present invention relates to a device and a method for testing a vehicle, in particular a motor vehicle, with the aid of sound and video sensors.

BACKGROUND INFORMATION

Automated optical inspection of motor vehicles with the aid of video cameras is available.

An object of the present invention is to provide an improved device and an improved method for the automated testing of vehicles, in particular motor vehicles.

This object may be achieved by an example method and example device according to the present invention.

The example method according to the present invention for testing a vehicle includes driving the vehicle over a measuring device, and recording the sound emitted by the vehicle during the drive-over using a sound recording device (microphone) and evaluating the recorded sound for vehicle diagnosis.

An example device according to the present invention for testing a vehicle has at least one sound recording device and one evaluation device. The sound recording device is designed for recording sound which is generated and emitted by a vehicle to be tested. The evaluation device is designed for evaluating the sound recorded by the at least one sound recording device for vehicle diagnosis.

An example method according to the present invention and an example device according to the present invention may make improved vehicle diagnosis possible by evaluating the sound emitted by the vehicle to be tested and identifying abnormalities in this sound which point to an error of the vehicle.

The automated recording and evaluation of sound which is emitted during operation of the motor vehicle by the engine, the exhaust system and/or the articulations, are presently not heretofore known.

A motor vehicle diagnosis according to the present invention may be carried out reliably and in automated form. The result is in particular not dependent on the skills and the experience of a motor vehicle mechanic carrying out the diagnosis, who evaluates the noises emitted by the vehicle "by ear."

In one specific embodiment, a method according to the present invention includes comparing the recorded sound with a predefined setpoint sound and identifying deviations of the recorded sound from the predefined setpoint sound. An ideal, perfectly functioning vehicle generates setpoint sound, which in particular includes the noises of the running internal combustion engine, including the exhaust gas system, caused by possible vibrations of components on the vehicle and the noise of the rolling motion of the tires.

Defects in the internal combustion engine or the exhaust gas system, unfastened or loose components and/or defective tires cause additional noises or deviating noises in the actual sound, so that this sound deviates from a setpoint sound which is emitted by an ideal vehicle having no defects. This makes it possible to detect defects in the vehicle by determining the difference between the recorded actual sound and the predefined, ideal setpoint sound.

In one specific embodiment, the evaluation of the recorded sound includes identifying abnormalities in the recorded sound. This makes an automated vehicle diagnosis possible even when the setpoint sound of an ideal vehicle is not known. Abnormalities may be identified, for example, with the aid of so-called statistical learning methods.

In one specific embodiment, the method includes recording at least one optical image of the vehicle and optically representing at least one located sound source in at least one recorded image. This makes it possible to locate sound sources which are possibly caused by defects particularly well and conveniently. The combination of the acoustic evaluation with optical images of the vehicle makes it possible to improve and simplify the evaluation and error diagnosis even further, since it is directly identifiable in the combined image at which point of the vehicle the troubleshooting is be continued.

In one specific embodiment, the method includes locating at least one sound source on the vehicle. Locating the source(s) of noises contained in the recorded sound, e.g., with the aid of directional microphones, makes it possible to improve the quality of the diagnosis, since the sound sources and accordingly defects, which generate unusual noises, may be spatially located. The further troubleshooting may then be concentrated on the identified located and spatially limited area.

In one specific embodiment, a device according to the present invention has at least two sound recording devices (microphones). A plurality of sound recording devices makes it possible to locate the sound sources on the vehicle in a particularly good and effective manner.

In one specific embodiment, the sound recording devices are designed in such a way that good locating of the sources of the recorded sound is made possible. The sound recording devices may in particular be designed as directional microphones. By locating the sound sources precisely, the causes of possible defects may be narrowed down particularly well, and the troubleshooting is simplified and accelerated.

In one specific embodiment, a device according to the present invention includes at least one image recording device, which is designed for recording at least one image of the vehicle to be tested.

In one specific embodiment, a device according to the present invention includes an evaluation device, which is designed for representing the source(s) of the recorded sound in at least one image of the vehicle to be tested.

The present invention is explained below based on the figures.

DETAILED DESCRIPTION OF EXAMPLE EMBODIMENTS

Figure 1:
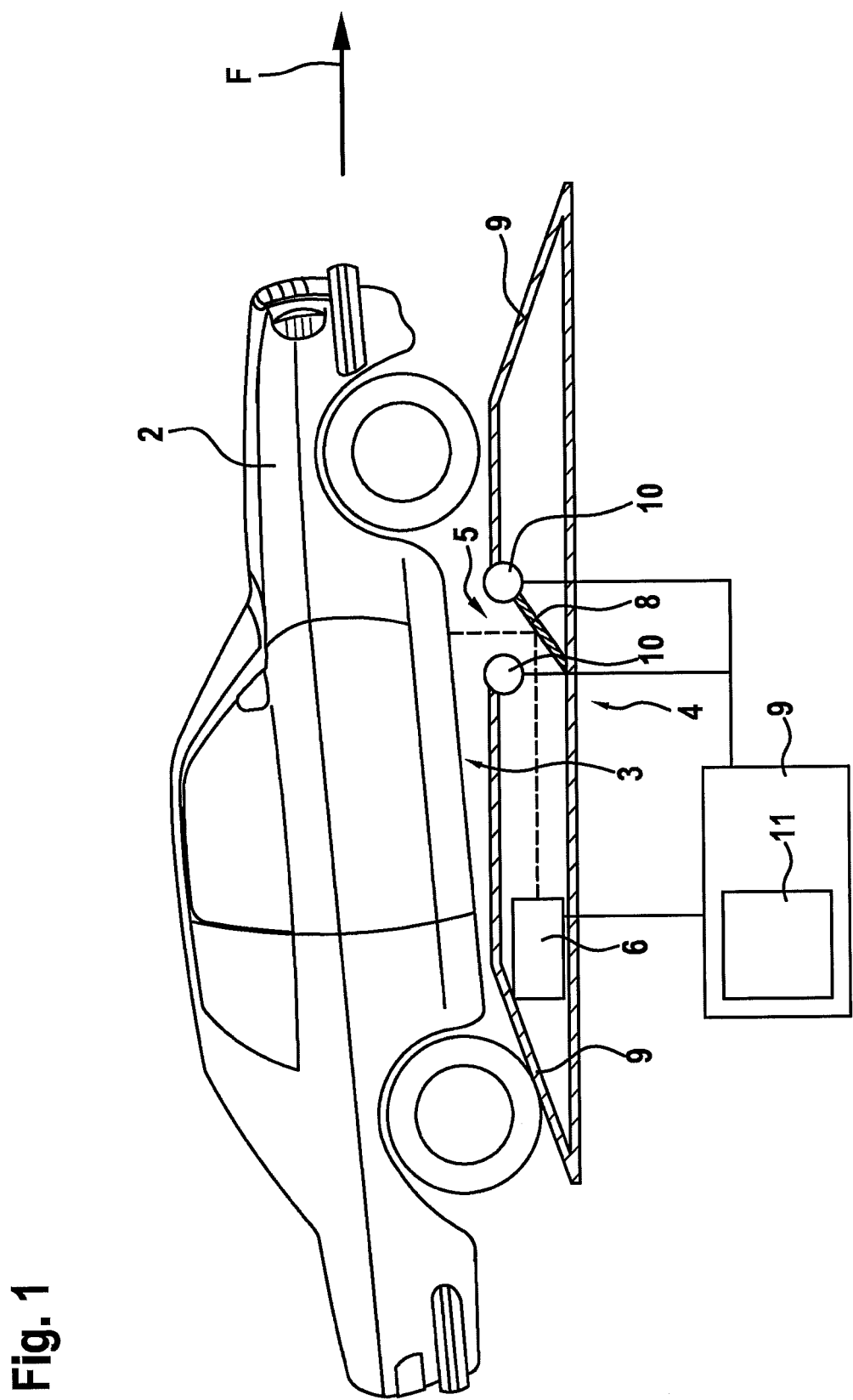
FIG. 1 shows a schematic side view of an example device according to the present invention including a motor vehicle to be tested.

FIG. 1 shows a schematic side view of a device 4 according to the present invention including a motor vehicle 2 to be tested.

A device 4 according to the present invention is designed as a trapezoid in cross section and has inclined end areas 9, which are used as ramps, and allow a motor vehicle 2 to be tested to drive over device 4.

An optical camera 6 and a mirror 8 are situated in the interior of device 4 in such a way that an image of at least one subarea of undercarriage 3 of motor vehicle 2 is projected by mirror 8 into camera 6. For this purpose, at least one opening 5 or a transparently designed area is provided in the upper surface of device 4, which, with the aid of mirror 8 makes an optical line of sight possible between camera 6 and undercarriage 3 of vehicle 2. In addition, illumination devices, which are not shown in FIG. 1, may be provided for sufficiently illuminating undercarriage 3 of motor vehicle 2.

Adjacent to opening 5 or the transparent area in the upper surface of device 4, sound recording devices 10 are provided which are designed for recording the sound emitted by vehicle 2 during the drive-over over device 4.

Sound recording devices 10 may be designed in particular as directional microphones 10, which record the sound from only a spatially limited area and thus make good locating of sound sources on motor vehicle 2 possible.

Sound recording devices 10 and camera 6 are connected to an evaluation device 9, which evaluates the signals provided by camera 6 and sound recording devices 10, in order to represent the recorded sound or the detected sound sources on a display device 11 and/or to detect possible errors in motor vehicle 2 based on the recorded sound.

Figure 2:
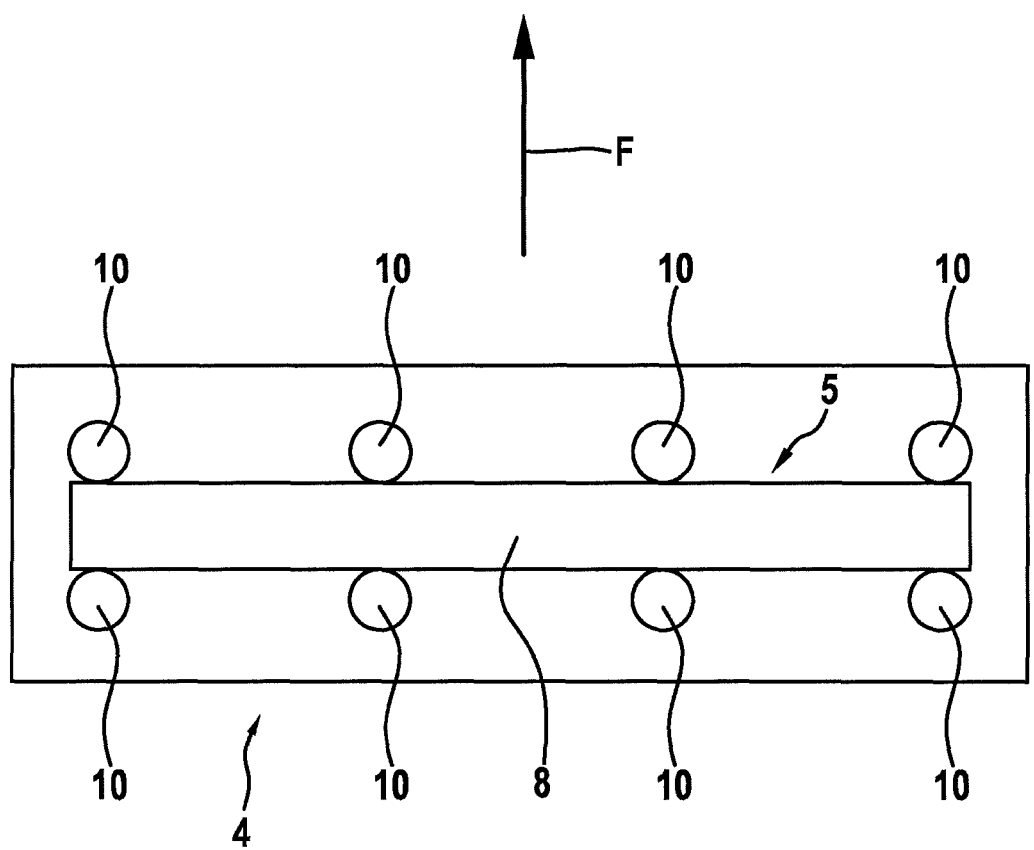
FIG. 2 shows a schematic top view of an example device according to the present invention.

FIG. 2 shows a schematic top view of the area of a device 4 according to the present invention in the surroundings of opening 5 or the transparent area, which is formed in the upper surface of device 4. The direction of travel of the vehicle during the drive-over over device 4 according to the present invention is represented by an arrow denoted as F.

Recognizable through opening 5 is mirror 8, which projects a strip-like section of undercarriage 3 of vehicle 2 into camera 6, the strip-like section in each case running transverse to direction of travel F. For example, a black and white camera 6, a color image camera 6 or a thermal imaging camera 6 may be used as camera 6.

Strip-like images of undercarriage 3 of vehicle 2 are recorded by camera 6 at a frequency which is dependent on the speed of vehicle 2 while driving over device 4 according to the present invention.

The strip-like images of undercarriage 3 of vehicle 2 recorded by camera 6 are combined by evaluation device 9 into an overall image of the undercarriage 3 of vehicle 6.

Around opening 5 are situated multiple sound sensors 10 which are designed for recording the sound emitted by vehicle 2 when driving over device 4.

The sound signals generated from the recorded sound by sound sensors 10 are forwarded to evaluation device 9 for further processing. Evaluation device 9 combines the sound signals with the image of undercarriage 3 of motor vehicle 2 which was composed of the images recorded by camera 6 and/or identifies suspicious noises in the recorded sound which indicate an error in vehicle 2. A combination of the optical image with an optical representation of the recorded sound or suspicious noises is displayed on display device 11.

To make possible a proper combination of the sound recorded by sound sensors 10 with images 12a, 12b, 12c recorded by camera 6, sound sensors 10 are calibrated with respect to camera 6.

Figure 3:
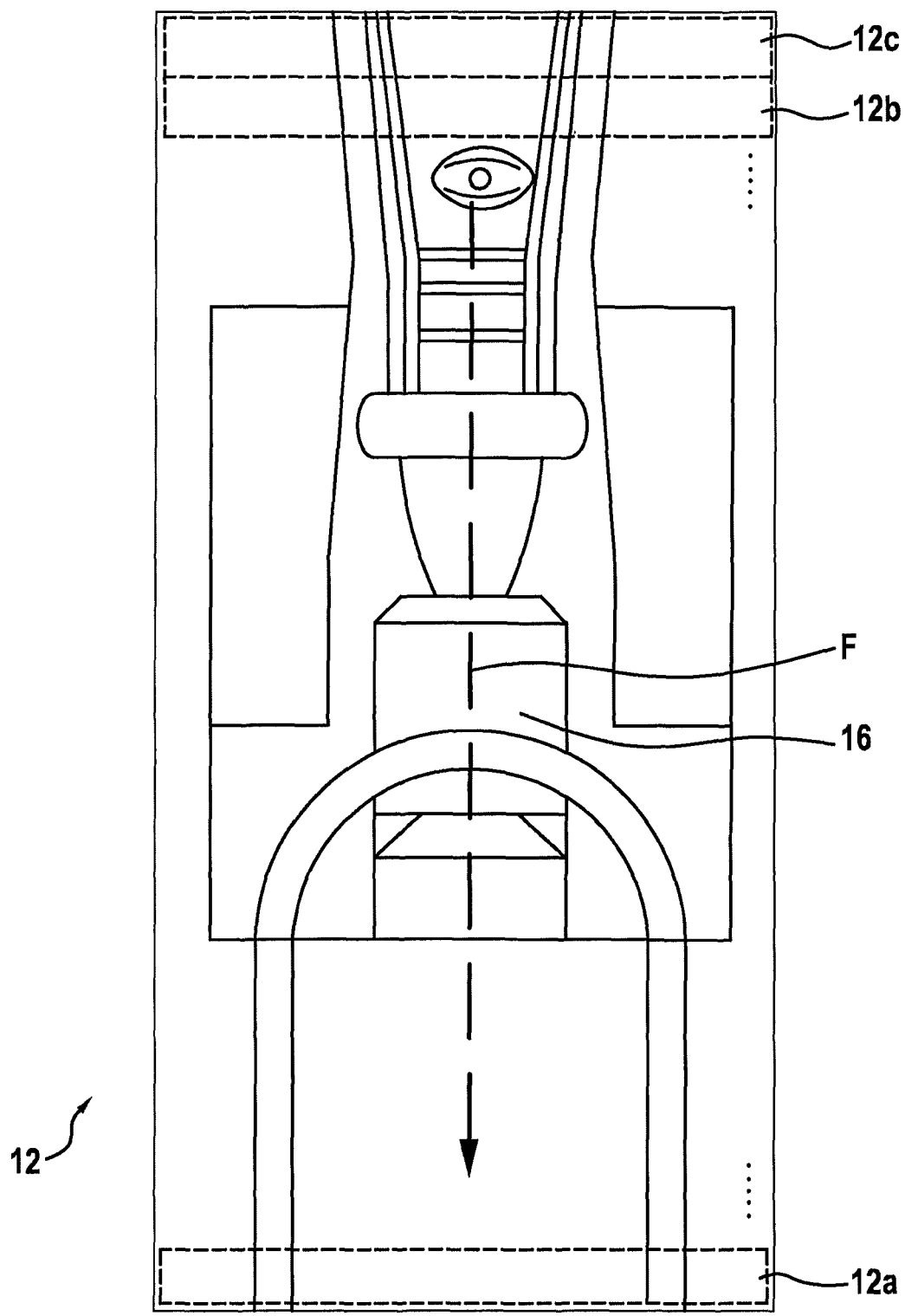
FIG. 3 shows a schematic diagram of an image of the undercarriage of a motor vehicle which was recorded using an example device according to the present invention.

FIG. 3 shows a schematic representation of an overall image 12 of undercarriage 3 of vehicle 2, overall image 12, as described above, being composed of a number of strip-like images 12a, 12b, 12c, not all of which are shown in FIG. 3.

Figure 4:
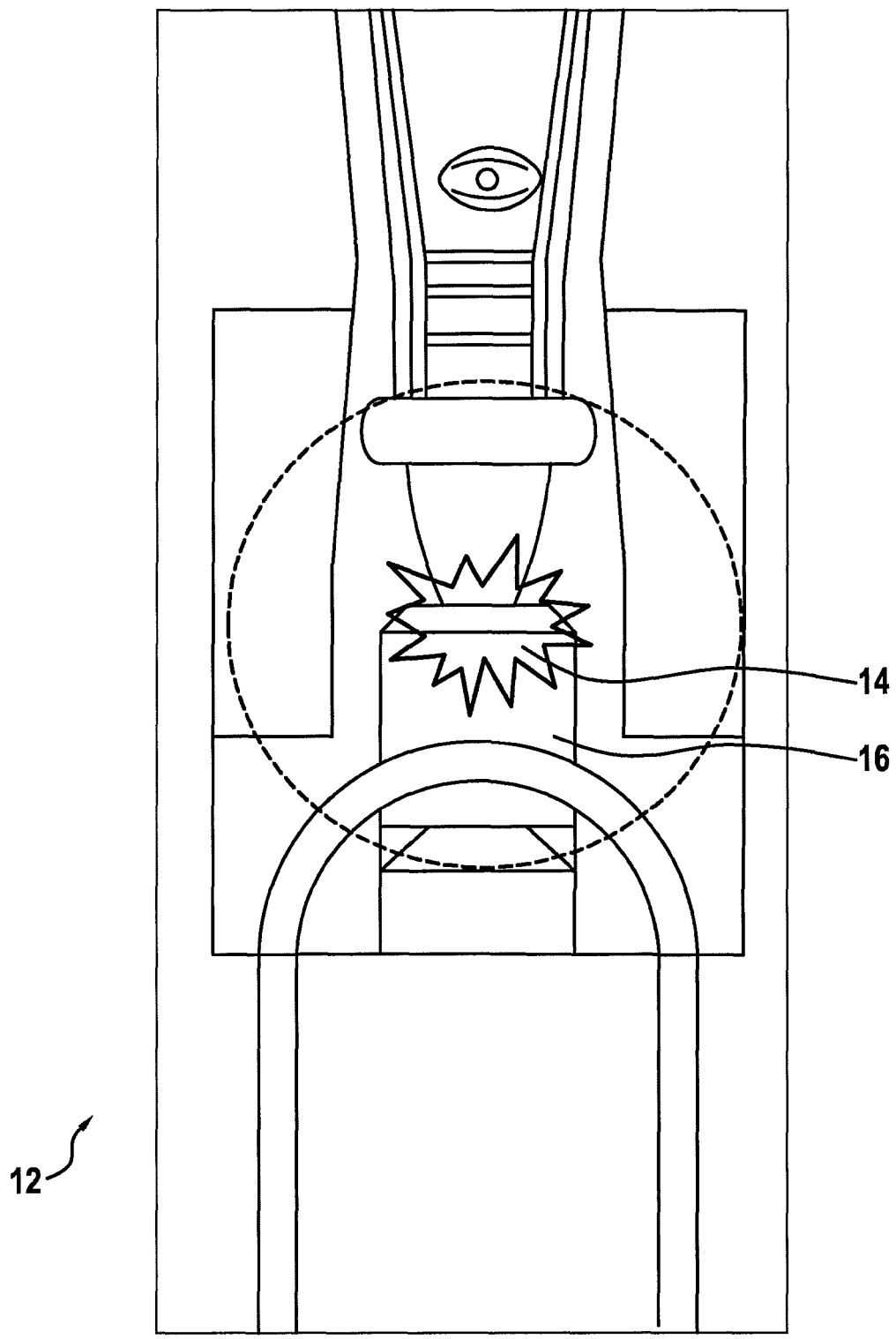
FIG. 4 shows a schematic diagram of an image of the undercarriage of a motor vehicle which was recorded using an example device according to the present invention, in which the position of an identified sound source is optically represented.

FIG. 4 shows overall image 12 of undercarriage 3 of vehicle 2, which was shown already in FIG. 3, in a schematic representation, location 14 of a source of a sound or noise identified by evaluation device 9 as suspicious being represented additionally.

By observing combined overall image 12 shown in FIG. 4, which is represented on display device 11 connected to evaluation device 9, a mechanic inspecting motor vehicle 2 is able to detect immediately the location at which a suspicious noise occurs, in order to continue with the troubleshooting. In the example shown in FIG. 4, the suspicious noise occurs in exhaust system 16 of motor vehicle 2, so that the mechanic continues the further troubleshooting preferably with a more detailed inspection of exhaust system 16.

Employing an example method according to the present invention and using the example device according to the present invention may simplify and accelerates the troubleshooting.

Combining video and sound images in a common representation makes it possible to increase the robustness with respect to the detection of defects in motor vehicles 2, which is also helpful for a possible further automation of the inspection process.

Taking the difference between the recorded actual noise level and a predefined setpoint noise level makes it possible to detect deviations in the sound image of the motor vehicle simply and rapidly. Alternatively, the evaluation based on the detection of abnormalities in the noise image of the motor vehicle may be carried out, for example, by a so-called statistical learning method.

The system of camera 6 and sound sensors 10 shown in FIGS. 1 and 2 is only exemplary. Of course, other systems are also possible which make simultaneous recording of images of undercarriage 3 of a motor vehicle 2 and the sound emitted by motor vehicle 2 possible.

In particular, device 4 may be entirely situated, for example, in a pit below the workshop level instead of the trapezoidal structure shown in FIG. 1.

The speed at which vehicle 2 is moved during the measurement over device 4 according to the present invention may be predefined and monitored by a speed measuring device in order to specify a defined optical and acoustic image for the case of an ideal, non-defective vehicle 2.

The sound recorded by sound sensors 10 may be evaluated and represented as a function of the particular sound volume and/or the particular frequency. For example, the recorded sound image may be examined for unusual frequencies which indicate defects in vehicle 2.

In displayed combined image 12, the sound sources may be represented differentiated in terms of color based on their sound volume and/or their frequency level in order to facilitate the analysis.

In particular in the case of superpositions of different noises, an evaluation according to the present invention is more reliable than the evaluation previously made by the mechanic "by ear."

What is claimed is:

1. A method for testing a motor vehicle, comprising:
providing a measuring device to be driven over by the vehicle;
detecting, by a plurality of directional microphones in the measuring device, a sound emitted by the vehicle during the drive-over of the measuring device;
recording the detected sound; and evaluating the recorded sound to detect an abnormal characteristic in the sound and in order to determine a location of an abnormality in the vehicle corresponding to a location on the vehicle from which the sound containing the abnormal characteristic is emitted, wherein the recording of the optical image includes:

recording a plurality of strip-shaped images corresponding to different portions of an undercarriage of the vehicle, and composing the single image as a combination of the strip-shaped images.

2. The method as recited in claim 1, further comprising:
recording at least one optical image of the vehicle and representing the location of the emitted sound on the vehicle in the recorded optical image.

3. The method as recited in claim 2, wherein each strip-shaped image corresponds to a different portion of the undercarriage that is consecutively exposed to a camera through an opening in the measuring device as the vehicle travels over the opening.

4. The method as recited in claim 3, wherein the microphones are located around a perimeter of the opening in the measuring device.

5. The method as recited in claim 1, further comprising:
comparing the recorded sound with a predefined setpoint sound.

6. A device for testing a vehicle, comprising:
at least one sound recording device designed for recording sound emitted by of the vehicle to be tested, wherein the at least one sound recording device includes a plurality of directional microphones; and an evaluation device designed for evaluating the recorded sound to detect an abnormal characteristic in the sound and in order to determine a location of an abnormality in the vehicle corresponding to a location on the vehicle from which the sound containing the abnormal characteristic is emitted at least one image recording device designed for recording at least one optical image of at least one area of the vehicle to be tested, wherein:

the image recording device records a plurality of strip-shaped images corresponding to different portions of an undercarriage of the vehicle, and the image recording device composes the single image as a combination of the strip-shaped images.

7. The device for testing a vehicle as recited in claim 6, further comprising:
at least one display device designed for representing the location on the vehicle from which the sound is emitted in at least one optical image of the vehicle to be tested.

8. The device as recited in claim 6, wherein each strip-shaped image corresponds to a different portion of the undercarriage that is consecutively exposed to a camera through an opening in the device as the vehicle travels over the opening.

9. The device as recited in claim 8, wherein the microphones are located around a perimeter of the opening in the device.

* * * * *